US009364027B2

(12) United States Patent
Hon (10) Patent No.: US 9,364,027 B2
(45) Date of Patent: Jun. 14, 2016

(54) ELECTRONIC CIGARETTE (71) Applicant: FONTEM HOLDINGS 1 B.V., Amsterdam (NL)

(72) Inventor: Lik Hon, North Point (HK)

(73) Assignee: Fontem Holdings 1 B.V., Amsterdam (NL)

( * ) Notice: Subject to any disclaimer, the term of this patent is extended or adjusted under 35 U.S.C. 154(b) by 0 days.

(21) Appl. No.: 14/328,561

(22) Filed: Jul. 10, 2014

(65) Prior Publication Data

US 2014/0318560 A1 Oct. 30, 2014

Related U.S. Application Data (60) Continuation of application No. 13/921,582, filed on Jun. 19, 2013, now Pat. No. 8,910,641, which is a continuation of application No. 13/088,276, filed on Apr. 15, 2011, now Pat. No. 8,511,318, which is a division of application No. 10/547,244, filed as application No. PCT/CN2004/000182 on Mar. 8, 2004, now abandoned.

(30) Foreign Application Priority Data

Apr. 29, 2003  (CN) .................................. 03 1 11582

(51) Int. Cl.
*A24F 47/00*  (2006.01)
*A61K 9/00*  (2006.01)

(52) U.S. Cl.
CPC ............ *A24F 47/008* (2013.01); *A24F 47/002* (2013.01); *A61K 9/007* (2013.01)

(58) Field of Classification Search
CPC .................................................... A24F 47/008
USPC ....................... 131/270; 128/202.21
See application file for complete search history.

(56) References Cited

U.S. PATENT DOCUMENTS

| 1,775,947 | A | 9/1930 | Robinson |
| 2,057,353 | A | 10/1936 | Whittemore et al. |
| 2,545,851 | A | 3/1951 | Kardos |
| 2,696,382 | A | 12/1954 | Gelardin |
| 3,200,819 | A | 8/1965 | Gilbert |
| 3,340,647 | A | 9/1967 | Lathrop |

(Continued)

FOREIGN PATENT DOCUMENTS

| CA | 2562581 A1 | 10/2005 |
| CN | 2047485 U | 11/1989 |

(Continued)

OTHER PUBLICATIONS

Australian Patent Office, "Examination Report for Singapore Patent Application No. 200505930-8", May 4, 2006, 3.

(Continued)

*Primary Examiner* — Michael H Wilson
*Assistant Examiner* — Dionne Walls Mayes
(74) *Attorney, Agent, or Firm* — Perkins Coie LLP (57) ABSTRACT

An electronic cigarette comprises nicotine without harmful tar. The cigarette includes a shell, a cell, nicotine solution, control circuit, and an electro-thermal vaporization nozzle installed in the air suction end of the shell. The advantages of the present invention are smoking without tar, reducing the risk of cancer, the user still gets a smoking experience, the cigarette is not lit, and there is no fire danger.

17 Claims, 6 Drawing Sheets

(56) References Cited

U.S. PATENT DOCUMENTS

| | | |
|---|---|---|
| 3,479,561 A | 11/1969 | Janning |
| 3,551,643 A | 12/1970 | Plaisted |
| 4,207,457 A | 6/1980 | Haglund et al. |
| 4,228,925 A | 10/1980 | Mendelovich |
| 4,771,796 A | 9/1988 | Myer |
| 4,922,901 A | 5/1990 | Brooks |
| 4,945,929 A | 8/1990 | Egilmex |
| 4,945,931 A | 8/1990 | Gori |
| 4,947,875 A | 8/1990 | Brooks et al. |
| 5,060,671 A | 10/1991 | Counts |
| 5,080,114 A | 1/1992 | Rudolph |
| 5,095,921 A | 3/1992 | Losee |
| 5,144,962 A | 9/1992 | Counts et al. |
| 5,190,060 A | 3/1993 | Gerding et al. |
| 5,261,424 A | 11/1993 | Sprinkel |
| 5,269,327 A | 12/1993 | Counts |
| 5,505,214 A | 4/1996 | Collins |
| 5,666,977 A | 9/1997 | Higgins |
| 5,743,251 A | 4/1998 | Howell |
| 5,819,756 A | 10/1998 | Mielordt |
| 5,894,841 A | 4/1999 | Voges |
| 5,924,784 A | 7/1999 | Chliwnyj |
| 6,016,038 A | 1/2000 | Mueller |
| 6,040,560 A | 3/2000 | Fleischhauer et al. |
| 6,155,268 A | 12/2000 | Takeuchi |
| 6,178,969 B1 | 1/2001 | St. Charles |
| 6,196,218 B1 | 3/2001 | Voges |
| 6,211,626 B1 | 4/2001 | Lys |
| 6,234,167 B1 | 5/2001 | Cox |
| 6,443,146 B1 | 9/2002 | Voges |
| 6,459,919 B1 | 10/2002 | Lys |
| 6,491,516 B1 | 12/2002 | Tal |
| 6,501,052 B2 | 12/2002 | Cox |
| 6,532,965 B1 | 3/2003 | Abhulimen |
| 6,719,443 B2 | 4/2004 | Gutstein |
| 6,772,756 B2 | 8/2004 | Shayan |
| 6,854,470 B1 | 2/2005 | Pu |
| 7,300,178 B2 | 11/2007 | Helou |
| 7,997,280 B2 | 8/2011 | Rosenthal |
| 2004/0175521 A1 | 9/2004 | Nakamura |
| 2004/0182403 A1 | 9/2004 | Andersson et al. |
| 2005/0016550 A1 | 1/2005 | Katase |

FOREIGN PATENT DOCUMENTS

| | | |
|---|---|---|
| CN | 1196660 A | 10/1998 |
| CN | 2293957 Y | 10/1998 |
| CN | 1233436 | 11/1999 |
| CN | 1530041 | 9/2004 |
| CN | 201797997 U | 4/2011 |
| CN | 202026802 U | 11/2011 |
| CN | 202026804 U | 11/2011 |
| EP | 0342538 A | 11/1989 |
| EP | 0430559 | 6/1991 |
| EP | 0295122 | 1/1992 |
| EP | 0295122 B1 | 1/1992 |
| EP | 0845220 | 6/1998 |
| GB | 1528391 A | 10/1978 |
| JP | 64-000498 U | 1/1989 |
| JP | 02-124082 A | 5/1990 |
| JP | 06-114105 A | 4/1994 |
| JP | 07-506999 T | 8/1995 |
| JP | 09-075058 A | 3/1997 |
| JP | 2984657 | 4/1999 |
| UA | 47514 C2 | 7/2002 |
| UA | 49831 | 5/2010 |
| WO | 9748293 | 12/1997 |
| WO | 0049901 A2 | 8/2000 |
| WO | 0050111 | 8/2000 |
| WO | 02098389 | 12/2002 |
| WO | 03034847 | 1/2003 |
| WO | 03016783 | 2/2003 |
| WO | 03022364 A | 3/2003 |
| WO | 03055486 A | 7/2003 |
| WO | 03096761 | 11/2003 |
| WO | 03101454 | 12/2003 |
| WO | 2004080216 A1 | 9/2004 |
| WO | 2004095955 A1 | 11/2004 |

OTHER PUBLICATIONS

Canadian Intellectual Property Office "Office Action for Canadian Patent Application No. 2,752,134", Feb. 1, 2013, 3.

Canadian Intellectual Property Office, "Office Action for Canadian Patent Application No. 2518174", Apr. 14, 2010, 4.

Canadian Intellectual Property Office, "Second Office Action for Canadian Patent Application No. 2,752,134", Dec. 12, 2013, 2.

Eurasian Patent Office, "Translation of Office Action for Eurasian Patent Application No. 200501704", Mar. 16, 2007, 1.

European Patent Office, "Supplementary European Search Report for European Patent Application No. 04718242", Jul. 27, 2007, 3.

European Patent Office, "Supplementary Partial European Search Report for European Patent Application No. 04718242", May 22, 2007.

Government of India Patent Office, "First Examination Report for Indian Patent Application No. 3794/DELNP/2005", Dec. 18, 2007, 2.

IP Australia, "Examiner's First Report on Patent Application No. 2004234199", Aug. 14, 2009, 3.

Israel Patent Office, "Hebrew Language Office Action for Israeli Patent Application No. 170872", May 22, 2008, 1.

Japanese Patent Office, "Office Action for Japanese Patent Application No. 2006-504199 with English translation", Oct. 30, 2009, 12.

Korean Intellectual Property Office, "Notice of Preliminary Rejection for Korean Patent Application No. 10-2005-7009767 with English translation", Jul. 27, 2009, 13.

Macau Patent Office, "Office Action and Search Report for Macau Patent Application No. I/121", Apr. 17, 2009, 14.

Malaysia Intellectual Property Office, "Examiner's Report for Malaysian Patent Application No. PI20041407", Sep. 28, 2007, 2.

Mexican Institute of Intellectual Property, "Spanish Language Office Letter for Mexican Patent Application No. PA/a/2005/009191", May 8, 2008, 2.

State Intellectual Property Office, "International Search Report for PCT/CN2004/000182", Jun. 10, 2004, 2.

Taiwan Patent Office, "English Translation of Official Letter including Search Report for Taiwanese Patent Application No. 093111573", Apr. 24, 2009, 3.

Ukraine Patent Office, "English Translation of Examination Report for Ukrainian Patent Application No. 200511258", Feb. 4, 2004, 2.

United States Patent and Trademark Office, "Final Office Action with Notice of References Cited for U.S. Appl. No. 13/921,582", Aug. 28, 2014, 9.

United States Patent and Trademark Office, "Non-Final Office Action for U.S. Appl. No. 10/547,244", Nov. 12, 2009, 7.

United States Patent and Trademark Office, "Non-Final Office Action for U.S. Appl. No. 10/547,244", Jul. 21, 2010, 7.

United States Patent and Trademark Office, "Non-Final Office Action for U.S. Appl. No. 13/921,582", Mar. 20, 2014, 7.

United States Patent and Trademark Office, "Non-Final Office Action with Notice of References Cited for U.S. Appl. No. 10/547,244", Jul. 26, 2011, 10.

United States Patent and Trademark Office, "Non-Final Office Action with Notice of References Cited for U.S. Appl. No. 13/088,276", May 21, 2012, 8.

United States Patent and Trademark Office, "Non-Final Office Action with Notice of References Cited for U.S. Appl. No. 13/548,659", Mar. 15, 2013, 8.

United States Patent and Trademark Office, "Notice of Allowance for U.S. Appl. No. 13/088,276", Apr. 15, 2013, 8.

United States Patent and Trademark Office, "Notice of Allowance with Notice of References Cited for U.S. Appl. No. 14/289,366", Sep. 11, 2014, 12.

Hewlett-Packard, Thermal Ink-Jet PrintCartridge Designers Guide (2nd Edition), available at least as early as Jan. 12, 1995.

NJOY, Inc. and related Defendants, Defendants' Invalidity Contentions, filed in *Fontem v. NJOY, Inc.* Consolidated Case No. CV 14-01645 GW (CD Cal) and Related Consolidated Cases, Feb. 26, 2015.

(56) References Cited

OTHER PUBLICATIONS

NJOY, Inc. and related Defendants, Exhibit A to Defendants' Invalidity Contentions—Invalidity Claim Chart for U.S. Pat. No. 8,910,641, Feb. 26, 2015.
NJOY, Inc. and related Defendants, Exhibit C to Defendants' Invalidity Contentions—Invalidity Claim Chart for U.S. Pat. No. 8,899,239, Feb. 26, 2015.
Collins, John M., Expert Report—Invalidity (Excerpts), CV14-01645, Jun. 18, 2015.
Collins, John M., Expert Report—Invalidity, CV14-01645-Appendix L-'239, Jun. 18, 2015.
Collins, John M., Expert Report—Invalidity, CV14-01645-Appendix M-1-'6419, Jun. 18, 2015.
Collins, John M., Expert Report—Invalidity, CV14-01645-Appendix M-2-'641, Jun. 18, 2015.
Collins, John M., Expert Report—Invalidity, CV14-01645-Appendix M-3-'641, Jun. 18, 2015.
Collins, John M., Expert Report—Invalidity, CV14-01645-Appendix M-4-'641, Jun. 18, 2015.
NJOY, Inc. et al., Petition for Inter Partes Review of U.S. Pat. No. 8,899,239—IPR2015-01304, May 29, 2015.
NJOY, Inc. et al., Petition for Inter Partes Review of U.S. Pat. No. 8,899,239—IPR2015-01304, Ex. 1001, U.S. Pat. No. 8,899,239, May 29, 2015.
NJOY, Inc. et al., Petition for Inter Partes Review of U.S. Pat. No. 8,899,239—IPR2015-01304, Ex. 1002, Declaration Dr. Samir Nayfeh, Ph.D. ("Nayfeh Decl."), May 29, 2015.
NJOY, Inc. et al., Petition for Inter Partes Review of U.S. Pat. No. 8,899,239—IPR2015-01304, Ex. 1003, Chinese Patent Publication No. 1233436A ("Hongbin"), May 29, 2015.
NJOY, Inc. et al., Petition for Inter Partes Review of U.S. Pat. No. 8,899,239—IPR2015-01304, Ex. 1004, U.S. Pat. No. 5,819,756 ("Mielordt"), May 29, 2015.
NJOY, Inc. et al., Petition for Inter Partes Review of U.S. Pat. No. 8,899,239—IPR2015-01304, Ex. 1005, U.S. Pat. No. 6,234,167 ("Cox"), May 29, 2015.
NJOY, Inc. et al., Petition for Inter Partes Review of U.S. Pat. No. 8,899,239—IPR2015-01304, Ex. 1006, European Patent Publication No. 0845220 A1 ("Susa"), May 29, 2015.
NJOY, Inc. et al., Petition for Inter Partes Review of U.S. Pat. No. 8,899,239—IPR2015-01304, Ex. 1007, U.S. Pat. No. 6,196,218 ("Voges"), May 29, 2015.
NJOY, Inc. et al., Petition for Inter Partes Review of U.S. Pat. No. 8,899,239—IPR2015-01304, Ex. 1008, *Fontem Ventures, B.V., et al. v. NJOY, Inc. et al.*, Civ. No. 14-1645 Dkt. 133 (CD. Cal. May 7, 2015) (Markman Hearing/Claim Construction Order), May 29, 2015.
NJOY, Inc. et al., Petition for Inter Partes Review of U.S. Pat. No. 8,899,239—IPR2015-01304, Ex. 1009, *Fontem Ventures, B.V., et al. v. NJOY, Inc. et al.*, Civ. No. 14-1645 Dkt. 65 (CD. Cal. Jan. 29, 2015) (Rulings on Claim Construction), May 29, 2015.
NJOY, Inc. et al., Petition for Inter Partes Review of U.S. Pat. No. 8,899,239—IPR2015-01304, Ex. 1010, *Fontem Ventures, B.V., et al. v. NJOY, Inc. et al.*, Civ. No. 14-1645 Dkt. 93 (CD. Cal. Mar. 19, 2015) (Joint Claim Construction and Prehearing Statement), May 29, 2015.
NJOY et al., Petition for Inter Partes Review of U.S. Pat. No. 8,899,239—IPR2015-01304, Ex. 1011, *Fontem Ventures, B.V., et al. v. NJOY, Inc. et al.*, Civ. No. 14-1645 Dkt. 34 (CD. Cal. Sep. 30, 2014) (Revised Joint Claim Construction and Prehearing Statement), May 29, 2015.
NJOY, Inc. et al., Petition for Inter Partes Review of U.S. Pat. No. 8,899,239—IPR2015-01304, Ex. 1012, Patent Owner's Dictionary Definitions of "E-Cigarette" from related IPR proceedings, May 29, 2015).
NJOY, Inc. et al., Petition for Inter Partes Review of U.S. Pat. No. 8,899,239—IPR2015-01304, Ex. 1013, *Fontem Ventures, B.V., et al. v. NJOY, Inc. et al.*, Civ. No. 14-1645 Dkt. 95 (CD. Cal. Apr. 9, 2015) (Defendant's Opening Claim Construction Brief), May 29, 2015.
NJOY, Inc. et al., Petition for Inter Partes Review of U.S. Pat. No. 8,899,239—IPR2015-01304, Ex. 1014, *Fontem Ventures, B.V., et al. v. NJOY, Inc. et al.*, Civ. No. 14-1645 Dkt. 116 (CD. Cal. Apr. 23, 2015) (Defendant's Responsive Claim Construction Brief), May 29, 2015.
NJOY, Inc. et al., Petition for Inter Partes Review of U.S. Pat. No. 8,899,239—IPR2015-01304, Ex. 1015, *Fontem Ventures, B.V., et al. v. NJOY, Inc. et al.*, Civ. No. 14-1645 Dkt. 117 (CD. Cal. Apr. 23, 2015) (Plaintiffs' Responsive Claim Construction Brief), May 29, 2015.
NJOY, Inc. et al., Petition for Inter Partes Review of U.S. Pat. No. 8,899,239—IPR2015-01304, Ex. 1016, *Fontem Ventures, B.V., et al. v. NJOY, Inc. et al.*, Civ. No. 14-1645 Dkt. 117-2 (CD. Cal. Apr. 23, 2015) (Plaintiffs' Responsive Claim Construction Brief Exhibit 3), May 29, 2015.
NJOY, Inc. et al., Petition for Inter Partes Review of U.S. Pat. No. 8,899,239—IPR2015-01304, Ex. 1017, *Fontem Ventures, B.V., et al. v. NJOY, Inc. et al.*, Civ. No. 14-1645 Dkt. 117-2 (CD. Cal. Apr. 23, 2015) (Plaintiffs' Responsive Claim Construction Brief Exhibit 4), May 29, 2015.
NJOY, Inc. et al., Petition for Inter Partes Review of U.S. Pat. No. 8,899,239—IPR2015-01304, Ex. 1018, *Fontem Ventures, B.V., et al. v. NJOY, Inc. et al.*, Civ. No. 14-1645 Dkt. 117-2 (CD. Cal. Apr. 23, 2015) (Plaintiffs' Responsive Claim Construction Brief Exhibit 5), May 29, 2015.
NJOY, Inc. et al., Petition for Inter Partes Review of U.S. Pat. No. 8,899,239—IPR2015-01304, Ex. 1019, Declaration of Saurabh Gupta from IPR2014-01289, May 29, 2015.
NJOY, Inc. et al., Petition for Inter Partes Review of U.S. Pat. No. 8,899,239—IPR2015-01304, Ex. 1020, Curriculum Vitae of Dr. Samir Nayfeh, Ph.D., May 29, 2015.
NJOY, Inc. et al., Petition for Inter Partes Review of U.S. Pat. No. 8,899,239—IPR2015-01304, Ex. 1021, Abstract of Title for U.S. Pat. No. 6,234,167 ("Cox"), May 29, 2015.
NJOY, Inc. et al., Petition for Inter Partes Review of U.S. Pat. No. 8,899,239—IPR2015-01304, Ex. 1022, U.S. Pat. No. 5,666,977 ("Higgins"), May 29, 2015.
NJOY, Inc. et al., Petition for Inter Partes Review of U.S. Pat. No. 8,899,239—IPR2015-01304, Ex. 1023, U.S. Pat. No. 6,155,268 ("Takeuchi"), May 29, 2015.
NJOY, Inc. et al., Petition for Inter Partes Review of U.S. Pat. No. 8,899,239—IPR2015-01304, Ex. 1024, U.S. Pat. No. 5,505,214 ("Collins"), May 29, 2015.
NJOY, Inc. et al., Petition for Inter Partes Review of U.S. Pat. No. 8,899,239—IPR2015-01304, Ex. 1025, U.S. Pat. No. 2,545,851 ("Kardos"), May 29, 2015.
NJOY, Inc. et al., Petition for Inter Partes Review of U.S. Pat. No. 8,899,239—IPR2015-01304, Ex. 1026, U.S. Pat. No. 3,479,561 ("Janning"), May 29, 2015.
NJOY, Inc. et al., Petition for Inter Partes Review of U.S. Pat. No. 8,899,239—IPR2015-01304, Ex. 1027, U.S. Pat. No. 4,771,796 ("Myer"), May 29, 2015.
NJOY, Inc. et al., Petition for Inter Partes Review of U.S. Pat. No. 8,899,239—IPR2015-01304, Ex. 1028, U.S. Pat. No. 6,719,443 ("Gutstein"), May 29, 2015.
NJOY, Inc. et al., Petition for Inter Partes Review of U.S. Pat. No. 8,899,239—IPR2015-01304, Ex. 1029, U.S. Pat. No. 5,388,574 ("Ingebrethsen"), May 29, 2015.
NJOY, Inc. et al., Petition for Inter Partes Review of U.S. Pat. No. 8,910,641—IPR2015-01299, May 29, 2015.
NJOY, Inc. et al., Petition for Inter Partes Review of U.S. Pat. No. 8,910,641—IPR2015-01299, Ex. 1001, U.S. Pat. No. 8,910,641 ("the '641 patent"), May 29, 2015.
NJOY, Inc. et al., Petition for Inter Partes Review of U.S. Pat. No. 8,910,641—IPR2015-01299, Ex. 1002, Declaration Dr. Samir Nayfeh, Ph.D. ("Nayfeh Decl."), May 29, 2015.
NJOY, Inc. et al., Petition for Inter Partes Review of U.S. Pat. No. 8,910,641—IPR2015-01299, Ex. 1003, U.S. Pat. No. 6,155,268 ("Takeuchi"), May 29, 2015.
NJOY, Inc. et al., Petition for Inter Partes Review of U.S. Pat. No. 8,910,641—IPR2015-01299, Ex. 1004, U.S. Pat. No. 5,666,977 ("Higgins"), May 29, 2015.
NJOY, Inc. et al., Petition for Inter Partes Review of U.S. Pat. No. 8,910,641—IPR2015-01299, Ex. 1005, U.S. Pat. No. 3,200,819 ("Gilbert"), May 29, 2015.

(56) References Cited

OTHER PUBLICATIONS

NJOY, Inc. et al., Petition for Inter Partes Review of U.S. Pat. No. 8,910,641—IPR2015-01299, Ex. 1006, U.S. Pat. No. 5,388,574 ("Ingebrethsen"), May 29, 2015.
NJOY, Inc. et al., Petition for Inter Partes Review of U.S. Pat. No. 8,910,641—IPR2015-01299, Ex. 1007, U.S. Pat. No. 4,207,457 ("Haglund"), May 29, 2015.
NJOY, Inc. et al., Petition for Inter Partes Review of U.S. Pat. No. 8,910,641—IPR2015-01299, Ex. 1008, U.S. Pat. No. 5,743,251, May 29, 2015.
NJOY, Inc. et al., Petition for Inter Partes Review of U.S. Pat. No. 8,910,641—IPR2015-01299, Ex. 1009, U.S. Publication No. 2015/0020825, May 29, 2015.
NJOY, Inc. et al., Petition for Inter Partes Review of U.S. Pat. No. 8,910,641—IPR2015-01299, Ex. 1010, European Publication No. 0 845 220 A1 ("Susa"), May 29, 2015.
NJOY, Inc. et al., Petition for Inter Partes Review of U.S. Pat. No. 8,910,641—IPR2015-01299, Ex. 1011, *Fontem Ventures, B.V., et al. v. NJOY, Inc. et al.*, Civ. No. 14-1645 Dkt. 133 (C.D. Cal. May 7, 2015) (Markman Hearing/Claim Construction Order), May 29, 2015.
NJOY, Inc. et al., Petition for Inter Partes Review of U.S. Pat. No. 8,910,641—IPR2015-01299, Ex. 1012, *Fontem Ventures, B.V., et al. v. NJOY, Inc. et al.*, Civ. No. 14-1645 Dkt. 65 (C.D. Cal. Jan. 29, 2015) (Rulings on Claim Construction), May 29, 2015.
NJOY, Inc. et al., Petition for Inter Partes Review of U.S. Pat. No. 8,910,641—IPR2015-01299, Ex. 1013, *Fontem Ventures, B.V., et al. v. NJOY, Inc. et al.*, Civ. No. 14-1645 Dkt. 93 (C.D. Cal. Mar. 19, 2015) (Joint Claim Construction and Prehearing Statement), May 29, 2015.
NJOY, Inc. et al., Petition for Inter Partes Review of U.S. Pat. No. 8,910,641—IPR2015-01299, Ex. 1014, *Fontem Ventures, B.V., et al. v. NJOY, Inc. et al.*, Civ. No. 14-1645 Dkt. 34 (C.D. Cal. Sep. 30, 2014) (Revised Joint Claim Construction and Prehearing Statement), May 29, 2015.
NJOY, Inc. et al., Petition for Inter Partes Review of U.S. Pat. No. 8,910,641—IPR2015-01299, Ex. 1015, Patent Owner's Dictionary Definitions of "E-Cigarette" from related IPR proceedings, May 29, 2015.
NJOY, Inc. et al., Petition for Inter Partes Review of U.S. Pat. No. 8,910,641—IPR2015-01299, Ex. 1016, U.S. Pat. No. 6,196,218, May 29, 2015.
NJOY, Inc. et al., Petition for Inter Partes Review of U.S. Pat. No. 8,910,641—IPR2015-01299, Ex. 1017, U.S. Pat. No. 5,144,962, May 29, 2015.
NJOY, Inc. et al., Petition for Inter Partes Review of U.S. Pat. No. 8,910,641—IPR2015-01299, Ex. 1018, '641 Patent File History, Final Rejection (Aug. 28, 2014), May 29, 2015.
NJOY, Inc. et al., Petition for Inter Partes Review of U.S. Pat. No. 8,910,641—IPR2015-01299, Ex. 1019, Curriculum Vitae of Dr. Samir Nayfeh, Ph.D., May 29, 2015.
NJOY, Inc. et al., Petition for Inter Partes Review of U.S. Pat. No. 8,910,641—IPR2015-01299, Ex. 1020, Abstract of Title for U.S. Pat. No. 5,388,574, May 29, 2015.
State Intellectual Property Office, PRC China, Examination Decision on the Request for Invalidation for CN03212882.7, Dec. 25, 2007.
U.S. District Court, Central District of California, Western Division, Defendant NJOY, Inc.'s Memorandum of Points and Authorities in Support of Defendants' Motion for Leave to Amend Invalidity Contentions dated Jun. 29, 2015 and tiled in Consolidated Case No. CV 14-01645 GW (MRW) and related consolidated cases.
U.S. District Court, Central District of California, Western Division, Defendant NJOY, Inc.'s Declaration of Brent K. Yamashita in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 1 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 2 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 3 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 4 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 5 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Reply Brief in Support of Defendants' Motion for Leave to Amend Invalidity Contentions dated Jul. 13, 2015 and filed in Consolidated Case No. CV 14-01645 GW (MRW) and related consolidated cases.
U.S. District Court, Central District of California, Western Division, Defendant NJOY, Inc.'s production documents VLACHOS 0000061-72; Consolidated Case No. CV 14-01645 GW (MRW) and related consolidated cases.

ELECTRONIC CIGARETTE

This Application is a Continuation of U.S. patent application Ser. No. 13/921,582 filed Jun. 19, 2013 and now U.S. Pat. No. 8,910,641, which is a Continuation of U.S. patent application Ser. No. 13/088,276 filed Apr. 15, 2011 and now U.S. Pat. No. 8,511,318, which is a Division of U.S. patent application Ser. No. 10/547,244 filed Feb. 27, 2006 and now abandoned, which is the U.S. National Phase Application of International Patent Application No. PCT/CN2004/000182 filed Mar. 8, 2004, which claims priority to Chinese Patent Application No. 03111582.9 filed Apr. 29, 2003. These applications are incorporated herein by reference.

TECHNICAL FIELD

The invention relates to an electronic cigarette which contains only nicotine without tar.

BACKGROUND ART

Despite it is commonly known that "smoking is harmful to your health", the number of smokers worldwide is up to 1 billion, and the number is increasing every year. According to the statistical data from the World Health Organization, about 4.9 million people die of diseases caused by smoking each year. Although smoking may cause serious respiratory diseases and cancer, it remains extremely difficult for smokers to quit smoking completely.

The active ingredient in a cigarette is nicotine. During smoking, nicotine, along with a tar aerosol droplets produced in the burning cigarette, enters smoker's alveolus and is rapidly absorbed. After being absorbed into the blood of a smoker, nicotine then produces an effect on the receptors of the smoker's central nervous system.

Nicotine is a kind of alkaloid with low molecular weight. A small dose of nicotine is essentially harmless to human body and its half-life in blood is quite short. The major harmful substance in tobacco is tar, and the tar in tobacco is composed of thousands of ingredients, tens of which are cancerogenic substances. At present, it has been proven that passive smoking can be harmful to non-smokers.

Some cigarette substitutes that contain only nicotine without tar have been proposed, and many of them, such as "nicotine patch", "nicotine mouthwash", "nicotine chewing gum", "nicotine drink" etc., are made of pure nicotine. Although these cigarette substitutes are free from tar, their major disadvantage is that an effective peak concentration cannot be reached in the blood of a smoker due to slow absorption of nicotine. In addition, these cigarette substitutes cannot satisfy habitual smoking actions of a smoker, for example, inhaling action or sucking action, and thus are not likely to be widely accepted as effective substitutes for quitting smoking.

SUMMARY OF THE INVENTION

An objective of the present invention is to provide an electronic cigarette that overcomes the above-mentioned disadvantages and provides a cigarette that looks like a normal cigarette. The electronic cigarette, which is an integrated assembly resembling a cigarette holder, includes a shell, a cell, nicotine solution, a control circuit, a high temperature vaporization nozzle and accessories. An electro-thermal vaporization nozzle is arranged within an air suction end of the shell. The control circuit provides starting current to the electric heater within the vaporization nozzle. Under the high temperature in the vaporization nozzle, the liquid is rapidly vaporized to form a puff of smoke. The cell which provides power to the electric heater via the control circuit can be a disposable battery or a rechargeable battery.

The advantages of the present invention include smoking without tar, significantly reducing the cancerogenic risk. Furthermore, users still feel as if they are smoking, and the cigarette has no need to be lit and has no fire risk.

DETAILED DESCRIPTION OF THE INVENTION

Figure 1:
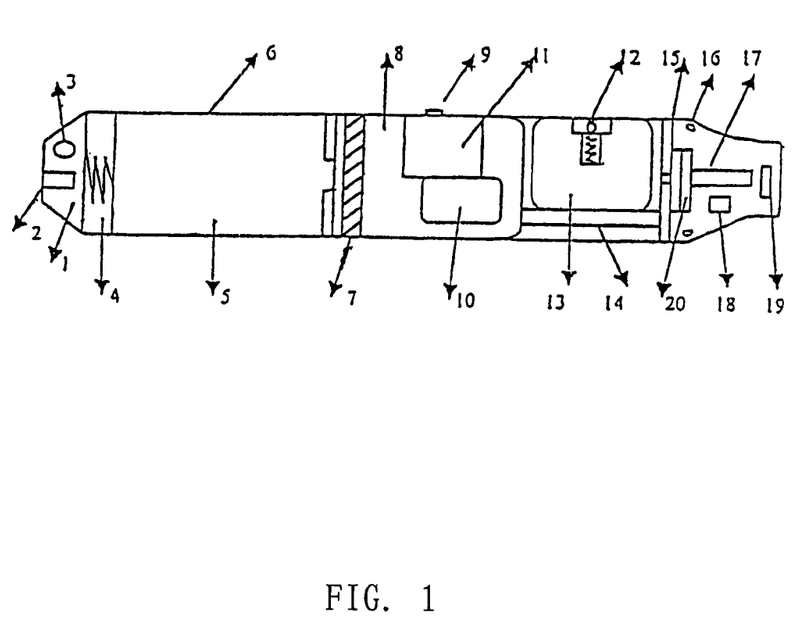
FIG. 1 is a structural diagram of the device in the first example in accordance with the present invention.
Figure 2:
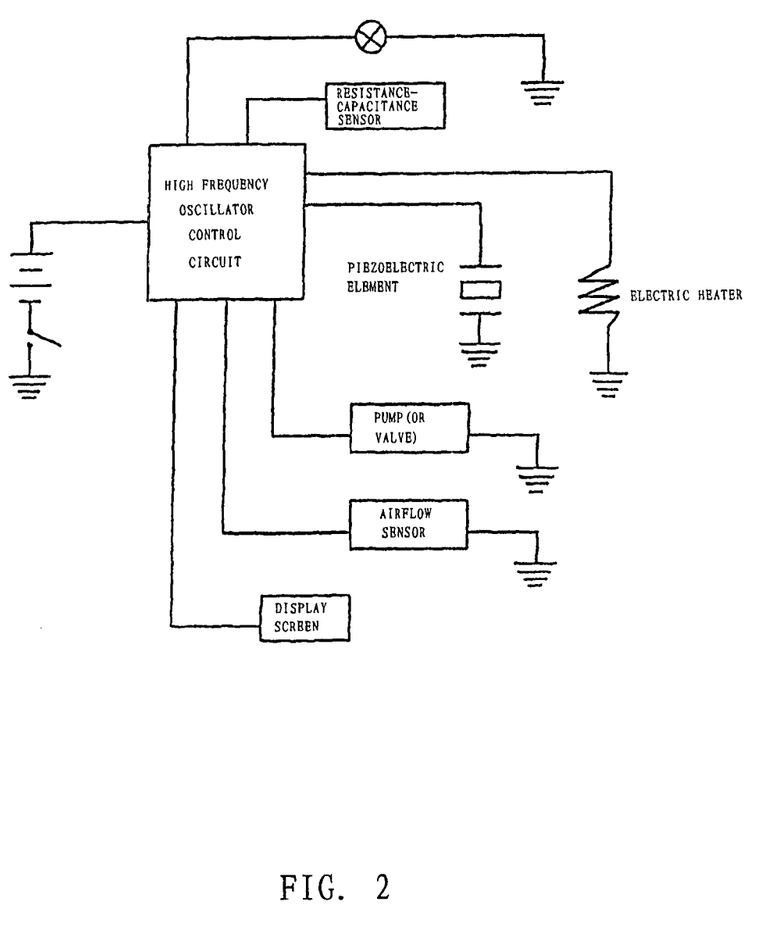
FIG. 2 is a block diagram of the circuit structure.

The high frequency generator of a control circuit board 8 is composed of a capacitance connecting three point type oscillator, an inductance connecting three point type oscillator, or a transformer-type oscillating circuit, which has the frequency of 35 KHz to 3.3 MHz. The circuit includes a automatic frequency fine-adjusting circuit resonating with a piezoelectric element 20. A nicotine solution storage container 13 is made of silicon rubber, alternatively, other polymers that can be protected against the penetration of nicotine can be used. A one-way valve for liquid injection 12 is sealed by a ball or cone member under the pressure of a spring. An airflow sensor 18 can be comprised of an array of integrated thermal sensitive resistors in the shape of film. The electrode of a resistance or capacitance sensor 19, which is sensitive to touches of human body, is composed of an upper metal film and a lower metal film and located at the end of the cigarette holder. The changes of the resistance or capacitance parameters due to human touch are inputted into the control circuit to perform the operation of a body sensitive switch.

The electric controlled pump 11, driven by a motor or a linear motor, drives a retarder that has a large speed ratio, via a shaft coupling, to revolve at a low speed but with large torque. The pump can be a peristaltic pump, a plunger pump, an eccentric pump or a screw pump. Alternatively, the liquid pump can use piezoelectric pump, a super magnetostrictive pump, a thermal expansion drive pump, a thermal contraction drive pump, a thermal bubble pump. The electric control pump or valve may be thermal contractible.

Figure 4:
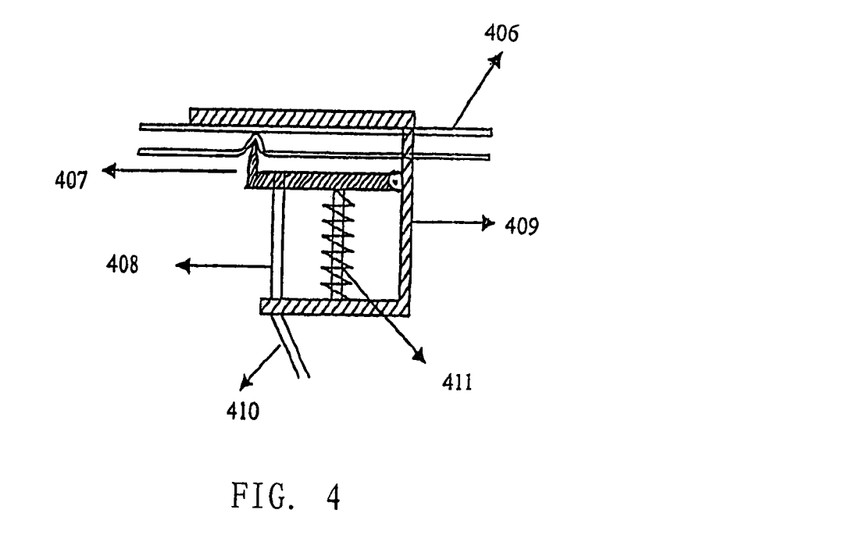
FIG. 4 is a schematic diagram of the valve made of memory alloy.

The valve is formed on a silicon rubber tube by nickel-titanium memory alloy or copper-based memory alloy under the force of electro-thermal contractions.

Figure 3:
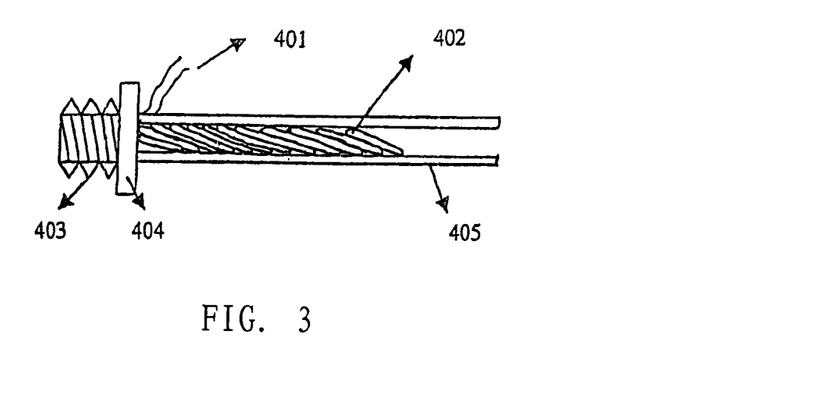
FIG. 3 is a schematic diagram of the structure of the high temperature vaporization nozzle and the electric-thermal element.

The electro-thermal vaporization nozzle 17 is made of high-temperature resistant materials with low thermal conductivity. The nozzle 17 is a tubule, with the internal diameter of 0.05-2 mm and the effective working length of 3-20 mm.

An electric heating element is provided within the nozzle, and the shapes of the electric heating element and the cavity of the nozzle are designed to facilitate vaporization and ejection of liquid. The vaporization nozzle 17 may be made of conventional ceramics, or be made of aluminum silicate ceramics, titanium oxide, zirconium dioxide, yttrium oxide ceramics, molten silicon, silicon dioxide, molten aluminum oxide. The vaporization nozzle 17 may be in the shape of straight tube or spiral, and may also be made from polytetrafluoethylene, carbon fiber, glass fiber or other materials with similar properties.

The electric heating element arranged within the vaporization nozzle 17 may be made of wires of nickel chromium alloy, iron chromium aluminum alloy, stainless steel, gold, platinum, tungsten molybdenum alloy, etc., and may be in the shape of straight line, single spiral, double spiral, cluster or spiral cluster, wherein the straight line and cluster are preferred. The heating function of the electric heating element may be achieved by applying a heating coating on the inner wall of the tube, and the coating may be made from electro-thermal ceramic materials, semiconductor materials, corrosion-resistant metal films, such as gold, nickel, chromium, platinum and molybdenum. The method for coating can include a coat sintering process, a chemical deposition sintering process and an ion spraying process. The materials mentioned above can be provided within the inner wall of vaporization nozzle in any of the processes mentioned above.

Figure 7:
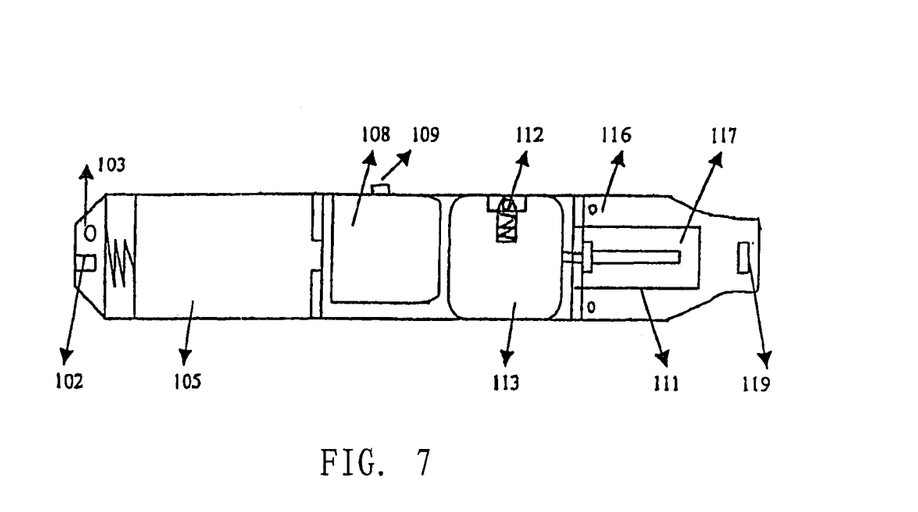
FIG. 7 is a structural diagram of the electronic cigarette in a second example.

The nozzle with high resistance, made of metal, can have no electric heating element being attached, and can be directly applied with heating current. Alternatively, the materials mentioned above can be arranged outside of the nozzle in any of the ways mentioned above, and an appropriate response time can also be achieved in the power supply mode of short-term preheating. Nicotine solution used in the atomization process comprises nicotine, propylene glycol, glycerol, organic acids, anti-oxidation agents, essence, water and alcohol, in which the nicotine content is 0.1%-6%, propylene glycol content 80%-90%, organic acids 0.2%-20%, the rest is glycerol, essence, anti-oxidation agents, water and alcohol.

Example 1

The Structural Diagram of the Device Shown in FIG. 1

When a smoker puts the cigarette holder on his/her mouth, the resistance sensor 19 activates the control circuit board 8. The control circuit board 8 then outputs two driving voltages respectively, one used to supply power to the electric heating element of the vaporization nozzle 17 and the other used to activate the micro pump 11 (shown in FIG. 6). The stored solution is then pumped to the nozzle 17 by the solution storage container 13. On the electric heating element of the nozzle 17, the nicotine solution is then vaporized into high temperature vapor which is subsequently ejected from the opening end. In the air, the vapor ejected out is then expanded and condensed into micro aerosol droplets.

The effect of the ultrasonic piezoelectric element 20 mounting on the nozzle is that, firstly, the large liquid droplets in the unstable thermal airflow under high pressure will be in sufficient contact with the electric heating element, and thereby be vaporized. Secondly, the liquid droplets in the nozzle 17 are directly fragmented and atomized. Thirdly, possible bumping when the liquid is above a boiling point will be avoided. The effect of integrated atomization will allow aerosol droplets with diameters of 0.2-3 um to enter into the alveolus easily and be absorbed. The airflow sensor 18 is sensitive to the diluted air which enters through air inlet 16 when a "suction" action take places. The sensed signals are transmitted to the control circuit, and the control circuit then stops supplying power to the micro pump and the electric heater after a certain time delay.

The relay relationship between the time delays of the micro pump and electric heater is as follows: after the electric heater is activated, the micro pump is activated after a time delay of 0.1-0.5 seconds; the electric heater is then turned off after a time delay of 0.2-0.5 seconds when the control circuit of the micro pump is turned off, so as to guarantee a complete vaporization of the liquid after quantitative liquid injection without any leftovers.

The nicotine solution container may be designed to be different sizes as required. The nicotine solution may be refilled once a day, or once a couple of days. The liquid crystal display screen 10 can show operating state parameters, such as cell capacity, smoking times per day, average using cycle and warnings for over smoking. A red LED 3 blinks for each smoking action, and a sawtooth wave signal that lasts for 1.2 seconds is given by the control circuit for blinking signals, which provides a gradual change of luminance to imitate the ignition and combustion process of a conventional cigarette. The charger 1, charging jack 2, spring 4, shell 6, threads 7, switch 9, passage tube 14 and baffle plate 15 are shown in FIG. 1. The silicon gel tube 601, pinch roller 602, worm 603 and motor 604 are shown in FIG. 6.

The control circuit and the ultrasonic micro pump may be integrated on one single chip by using a Micro Electronic Mechanical System (MEMS).

Example 2

The Simplified Electronic Cigarette

FIG. 7 is a structural diagram of the simplified device in which the ultrasonic atomization high frequency generator and the piezoelectric ceramic element 20 are omitted. To achieve a desirable atomization effect, tiny heating wires are used in combination with the nozzle (see FIG. 3), so that the maximum diameters of one or more vaporization cavities formed between the heating wire and the inner wall of the nozzle range from 0.02 mm to 0.6 mm. The function of the airflow sensor 18 omitted is replaced by the manner that the initial signal of the resistance or capacitance sensor 119 is delayed a certain time via the control circuit and acts as the ending signal. The electronic cigarette is configured as follows: the vaporization nozzle 117, the thermal drive pump 111 (see FIG. 5) made of nickel titanium memory alloy wire, and the liquid storage container 113 connected to the thermal drive pump constitute a liquid transmission system. Two outputs of the control circuit board 108 are respectively connected to the electric heater and the pump or valve. A body sensitive resistance sensor 119 is connected to the input of the control circuit. The cell 105 and red LED 103 are provided in the front end within the shell, and resemble a cigarette holder, a pipe or a pen.

The thermal drive pump is an electro-thermal shrinkable peristaltic pump, made of wires of nickel titanium memory alloy or copper based alloy, with gel tube which is pressed at three points respectively during the process of electro-thermal contraction to form a pressure cavity for pumping out liquid. The change of volume of the cavity within the thermal drive pump determines the quantity of the solution to be atomized each time. Upon contacting with user's mouth, the resistance sensor 119 activates the control circuit 108, the control circuit 108 then provides operating current to the thermal drive pump and the electric heater, and the output of the control circuit is turned off after the delay of 2 seconds for reactivation at the next smoking action. Alternatively, a thermal expansion drive pump or a thermal bubble pump is also applicable. The thermal expansion drive pump forms a pressure cavity for pumping out liquid by allowing a micro hydrogen container with an embedded electric heating element to block the liquid inlet and open the liquid outlet at the time of thermal expansion. The charging jack 102, LED 103, cell 105, switch 109, liquid-refilling valve 112 and air hole 116 are shown in FIG. 7.

Figure 5:
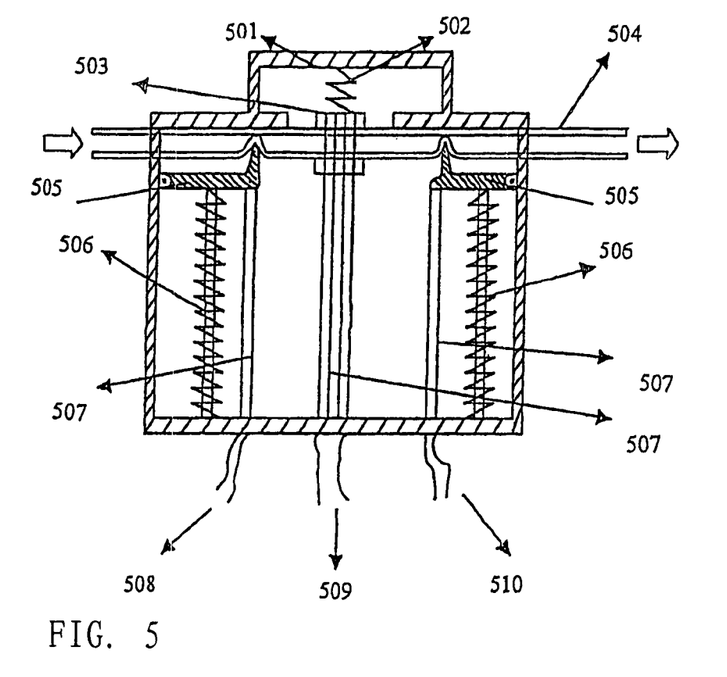
FIG. 5 is a schematic diagram of the peristaltic pump made of memory alloy.
Figure 6:
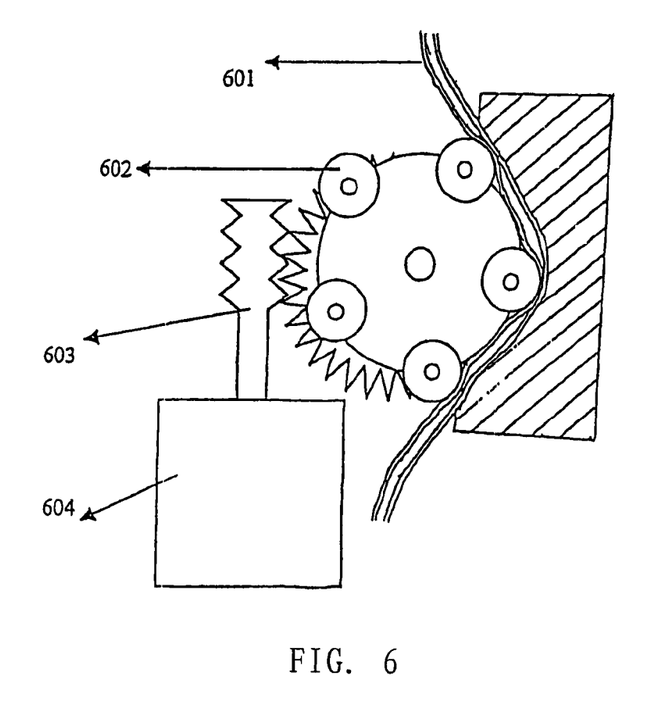
FIG. 6 is a schematic diagram of the peristaltic pump.

The electrode lead wire 401, heating wire 402, thread 403, base 404 and nozzle 405 are shown in FIG. 3. The support 501, extension spring 502, pumping-out pressure plate 503, silicon gel tube 504, stop pressure plate 505, supporting spring 506, memory alloy wire 507, electrode A 508, electrode B 509 and electrode 510 are shown in FIG. 5.

Example 3

The Electronic Cigarette Made of a Ni—Ti Memory Alloy

Figure 8:
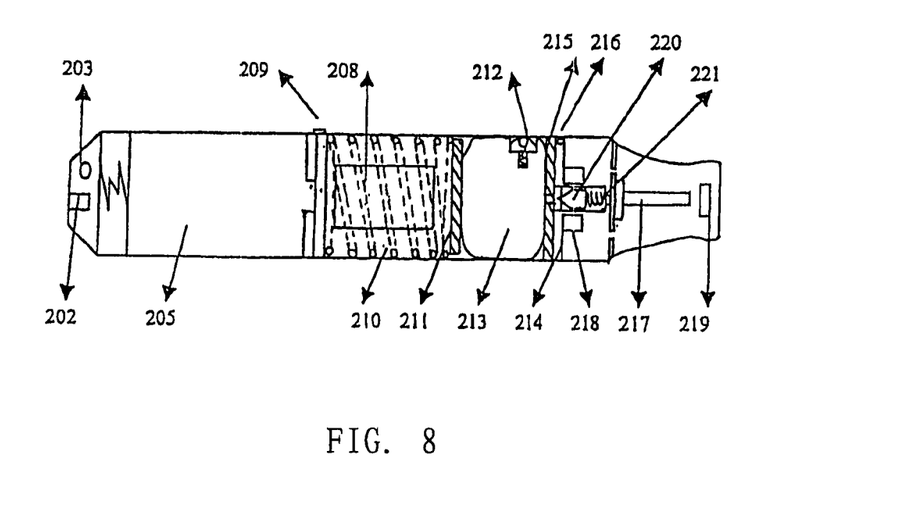
FIG. 8 is a structural diagram of the electronic cigarette in a third example.

FIG. 8 is a structural diagram of the electronic cigarette. The electro-thermal vaporization nozzle 217 of the device is connected to the liquid storage container 213 via a pneumatic valve 220. The super elastic member 210 is connected to the pressure plate 211 which is connected to the liquid storage container 213. The pneumatic valve is composed of a pneumatic film 214, a magnetic steel ring 218, a steel valve needle 220 and a reset spring 221. The super elastic member 210, which is made of Ni—Ti memory alloy, is used to apply a constant pressure on the liquid storage container via the pressure plate 211. When the pneumatic valve opens, the liquid with nicotine enters the vaporization nozzle from the liquid storage container via the pneumatic valve and is vaporized and condensed subsequently to form a puff of smoke at high temperature. Upon contacting with user's mouth, the resistance sensor activates the control circuit to supply power to the electric heater. When the user performs suction action, the Nd—Fe—B permanent magnetic alloy ring attracts the valve needle to move in response to the pneumatic film being subjected to negative pressure. Liquid is supplied when the valve needle opens, and after the pneumatic valve is reset, power supply to the electric heater is turned off after the delay of 0.5 seconds by the control circuit. The LED 203, charging jack 202, cell 205, control circuit 208, switch 209, refilling valve 212, baffle plate 215, air hole 216 and resistance sensor 219 are shown in FIG. 8.

Example 4

The Electronic Spray Cigarette Utilizing the Pressure of a Container

Figure 9:
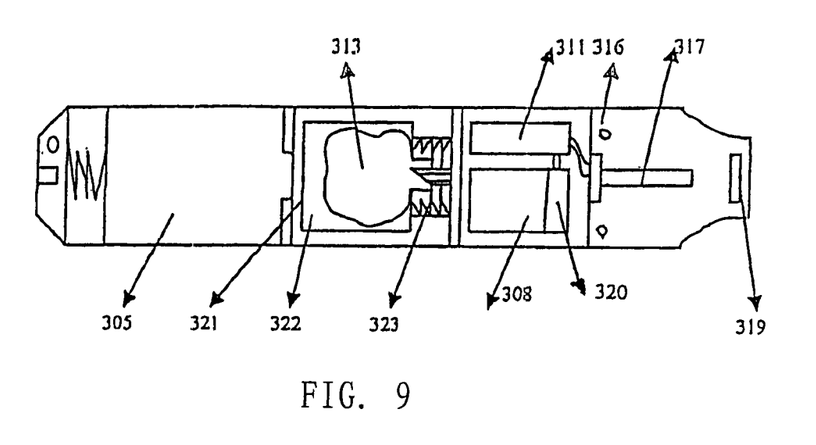
FIG. 9 is a structural diagram of the electronic cigarette in a fourth example.

In the device (see FIG. 9), the electro-thermal vaporization nozzle 317, the electronic valve 311 connected with the metering cavity 320, and the liquid storage container 313 form a liquid transmission passage. A gas vessel filled with high-pressure nitrogen is arranged around the periphery of the liquid storage container to exert pressure thereon to facilitate the transmission of the liquid. When a control signal is applied to the electronic valve, the electronic valve is activated, and the solution with nicotine enters the metering cavity from the liquid storage container under pressure. The solution pushes a piston so as to allow a constant volume of liquid at the other side of the piston to enter the vaporization nozzle via the electronic valve. The metering cavity provided at the valve is a cylinder having a liquid inlet and a liquid outlet. Located within the cylinder are the piston micro holes and the reset spring connected onto the piston. The control circuit which is activated by the resistance sensor 319 controls the states of the electronic valve and the electric heater respectively. Due to slow infiltration of the micro hole of the piston in the metering cavity and the force of the reset spring, the piston returns to its original position within 5-8 seconds after each atomization process. The cell 305, pressure vessel 321, pressure chamber 322, seal threaded-opening 323, control circuit board 308 and air hole 316 are showed in FIG. 9.

Figure 10:
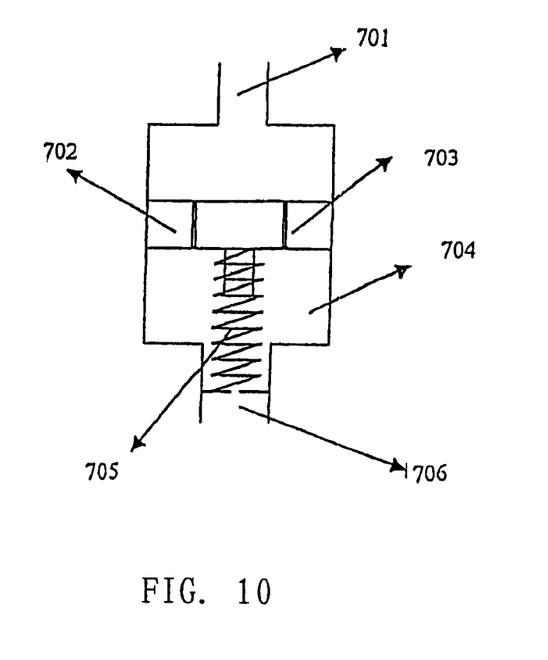
FIG. 10 is a structural diagram of the metering cavity in the fourth example.

The silicon gel tube 406, pressure-stopping plate 407, memory alloy wires 408, support 409, electrode lead wire 410 and pressure spring 411 are shown in FIG. 4. The inlet 701, piston 702, micro hole of the piston 703, metering cavity 704, reset spring 705 and outlet 706 are shown in FIG. 10.

The recipes of nicotine solution used are:

1. 6% nicotine, 85% propylene glycol, 2% glycerol, 2% essence, 1% organic acid and 1% anti-oxidation agent;
2. 4% nicotine, 80% propylene glycol, 5% glycerol, 1% butyl valerate, 1% isopentyl hexonate, 0.6% lauryl laurate, 0.4% benzyl benzoate, 0.5% methyl octynicate, 0.2% ethyl heptylate, 0.3% hexyl hexanoate, 2% geranyl butyrate, 0.5% menthol, 0.5% citric acid and 4% tobacco essence;
3. 2% nicotine, 90% propylene glycol, 2.5% citric acid, 1% essence and 4.5% tobacco essence;
4. 0.1% nicotine, 80% propylene glycol, 5% glycerol, 8% alcohol, 2.9% water, 1% essence, 1% tobacco essence and 2% organic acid.

The invention claimed is:

1. An electronic smoking device, comprising:
    a tubular housing having a first end and a second end;
    an outlet on the second end of the tubular housing;
    a wire coil in a tube, with the tube within the housing, and the wire coil configured to vaporize liquid moving from outside of the tube into the tube and contacting the wire coil;
    a control circuit in the tubular housing electrically connected to the wire coil and to a sensor;
    at least one air opening leading into the tubular housing, with the wire coil in between the at least one air opening and the second end of the tubular housing; and
    an LED at the first end of the tubular housing, with the LED electrically connected to the control circuit, and the LED configured to provide a gradual change in luminance to imitate a conventional cigarette.

2. The electronic smoking device of claim 1 with further comprising screw threads at the first end of the tubular housing.

3. The electronic smoking device of claim 1 with the tube comprising a fiber material.

4. The electronic smoking device of claim 1 wherein the housing resembles a cigarette.

5. The electronic smoking device of claim 1 with the wire coil parallel to the tubular housing.

6. The electronic cigarette of claim 1 with the LED configured to provide luminance that changes based on an output of the sensor.

7. The electronic smoking device of claim 1 with the tube attached to a first side of a base in the housing and further including screw threads on a second side of the base, opposite from the first side of the base.

8. An electronic smoking device, comprising:
    an electronic cigarette having a housing having a first end and a second end;
    an outlet on a second end of the housing;

a wire coil in a tube comprising a fiber material, with the tube in the housing and attached to a base in the housing, and with liquid in the housing moving from a location outside of the tube into contact with the wire coil in the tube to create vapor in the tube;

a control circuit in the housing electrically connected to the wire coil and to a sensor and a battery;

at least one air opening leading into the housing, with the wire coil in between the at least one air opening and the second end of the housing; and an LED at the first end of the housing, with the LED electrically connected to the control circuit, and the LED configured to provide a gradual change in luminance to imitate a conventional cigarette.

9. The electronic smoking device of claim 8 with the tube attached to a first side of the base and further including screw threads on a second side of the base, opposite from the first side of the base.

10. The electronic smoking device of claim 8 with the LED configured to provide a gradual change in luminance based on an output of the sensor.

11. The electronic smoking device of claim 8 wherein the housing resembles a cigarette.

12. An electronic smoking device, comprising:

an electronic cigarette having a housing having a first end and a second end;

an outlet on a second end of the housing;

a wire coil in a tube, with the tube in the housing and attached to a base in the housing;

a control circuit in the housing electrically connected to the wire coil and to a sensor and a battery in the housing;

an LED at the first end of the housing, with the LED electrically connected to the control circuit, and the LED configured to provide a gradual change in luminance via the control circuit;

at least one air opening leading into the housing, with the wire coil in between the at least one air opening and the second end of the housing.

13. The electronic smoking device of claim 12 with tube comprising a fiber material.

14. The electronic smoking device of claim 12 with the LED configured to provide a gradual change in luminance via the control unit that changes based on an output of the sensor.

15. The electronic smoking device of claim 12 wherein the housing resembles a cigarette.

16. An electronic cigarette, comprising:

a housing having a first section having a first end and a second section having a second end, with the first section attached to the second section;

an outlet at the second end of the second section of the housing;

a wire heating coil in a tube in the second section of the housing;

a control circuit electrically connected to the wire heating coil and to a sensor, and to a battery in the first section of the housing;

an LED at the first end of the first section of the housing, with the LED electrically connected to the control circuit, and the LED configured to provide luminance that changes based on an output of the sensor, to imitate a conventional cigarette; and at least one air opening leading into at least one of the first and second sections of the housing, with the wire heating coil in between the at least one air opening and the second end of the second section of the housing.

17. The electronic cigarette of claim 16 wherein the housing has a tubular first section attached to a tubular second section, and with the battery in the first section.

* * * * *